(12) United States Patent
Edlauer et al.

(10) Patent No.: US 8,104,477 B2
(45) Date of Patent: Jan. 31, 2012

(54) RADIOLUCENT FASTENING DEVICES FOR SECURING A PART OF A BODY DURING A MEDICAL PROCEDURE

(75) Inventors: Martin Edlauer, München (DE); Christian Radina, Garching (DE)

(73) Assignee: Brainlab AG, Feldkirchen (DE)

( * ) Notice: Subject to any disclaimer, the term of this patent is extended or adjusted under 35 U.S.C. 154(b) by 716 days.

(21) Appl. No.: 12/171,016

(22) Filed: Jul. 10, 2008

(65) Prior Publication Data
US 2009/0014011 A1 Jan. 15, 2009

Related U.S. Application Data

(60) Provisional application No. 60/948,712, filed on Jul. 10, 2007.

(30) Foreign Application Priority Data

Jul. 10, 2007 (EP) ..................................... 07112127

(51) Int. Cl.
*A61G 15/00* (2006.01)
*A61F 4/00* (2006.01)
*F16B 15/00* (2006.01)

(52) U.S. Cl. ........................ 128/845; 606/59; 411/498

(58) Field of Classification Search ............... 602/17, 602/18, 32, 33, 35, 36, 37; 606/54, 59, 61, 606/130, 62, 72, 56, 73, 104, 148, 232, 88, 606/98, 99, 297, 300–331; D24/127; 5/622, 5/640, 643; 623/13.11–13.2; 411/498, 383, 411/493, 497

See application file for complete search history.

(56) References Cited

U.S. PATENT DOCUMENTS

| 4,169,478 | A | * | 10/1979 | Hickmann | .................... 606/151 |
| 5,122,132 | A | * | 6/1992 | Bremer | ......................... 606/56 |
| 6,896,678 | B2 | * | 5/2005 | Tweardy | ....................... 606/916 |
| 2002/0042618 | A1 | | 4/2002 | Tweardy | |

FOREIGN PATENT DOCUMENTS

| EP | 1 026 513 | 8/2000 |
| EP | 1 598 028 | 11/2005 |
| WO | WO 2006/127392 | 11/2006 |

* cited by examiner

Primary Examiner — Patricia Bianco
Assistant Examiner — Tarla Patel
(74) Attorney, Agent, or Firm — Renner, Otto, Boisselle & Sklar, LLP

(57) ABSTRACT

The fastening device in accordance with the invention is directed to a pin for securing the position of a part of a body, (for example, a head) for medical procedures. The fastening device can have an improved geometry, can be made from materials including unsubstituted, monosubstituted or multisubstituted polyphenylene, and/or silicon nitride ceramic, and can be made of one or more pieces. The fastening device in accordance with the invention produces improved performance with respect to the criteria of biocompatibility, ability to be sterilized, resistance to mechanical stress, and reduced artifact creation in medical imaging methods.

15 Claims, 21 Drawing Sheets

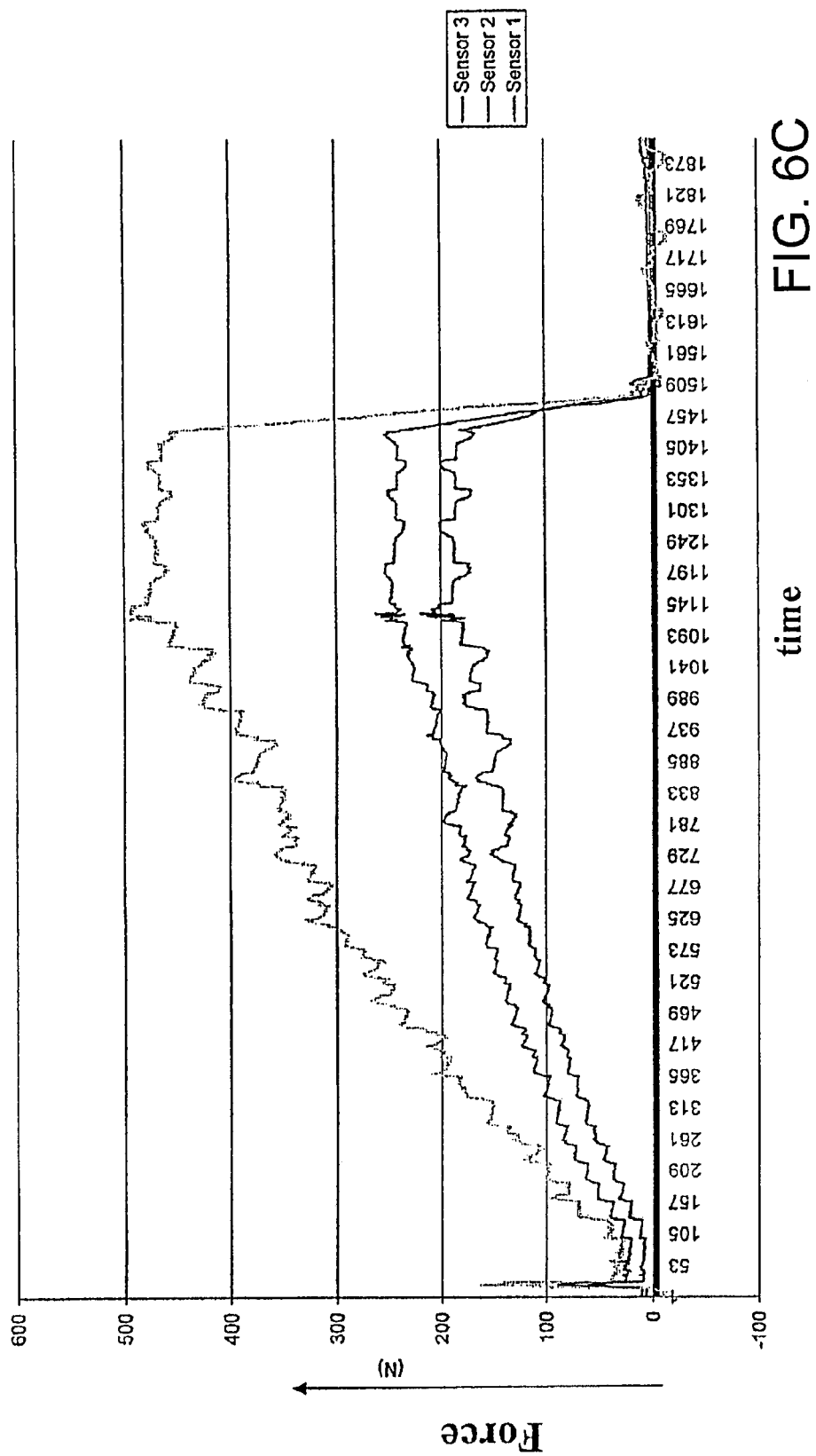

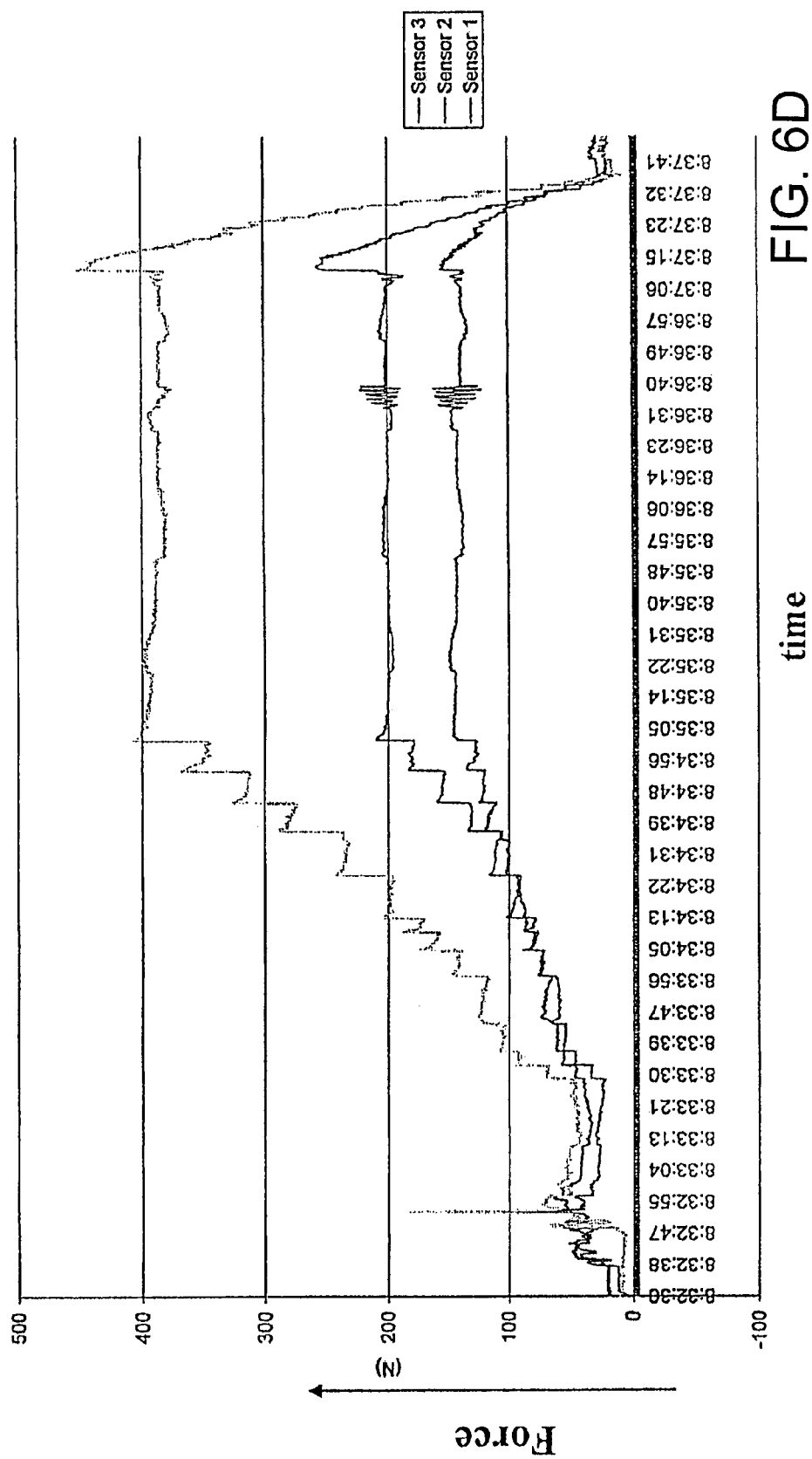

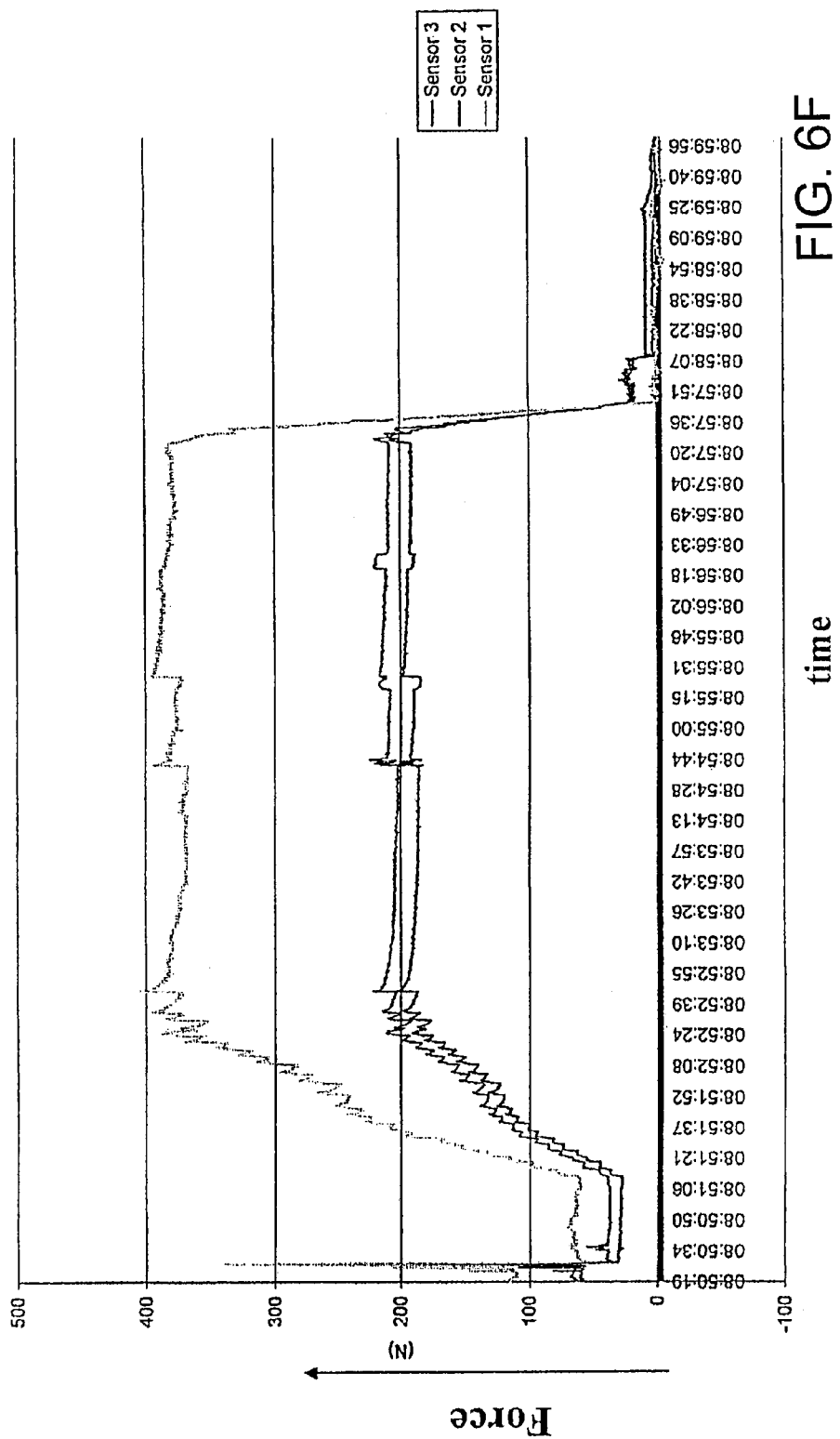

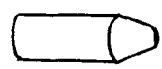 Pin 1
 Pin 1
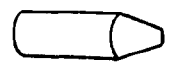 Pin 2
 Pin 2
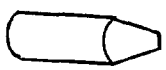 Pin 3
 Pin 3
FIG. 7A  FIG. 7B
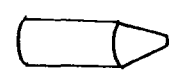 Pin 1
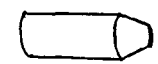 Pin 1
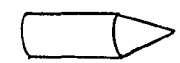 Pin 2
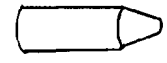 Pin 2
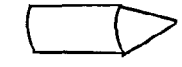 Pin 3
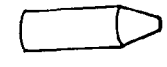 Pin 3
FIG. 7C  FIG. 7D
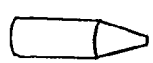 Pin 1
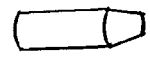 Pin 1
 Pin 2
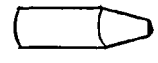 Pin 2
 Pin 3
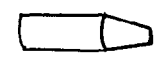 Pin 3
FIG. 7E  FIG. 7F

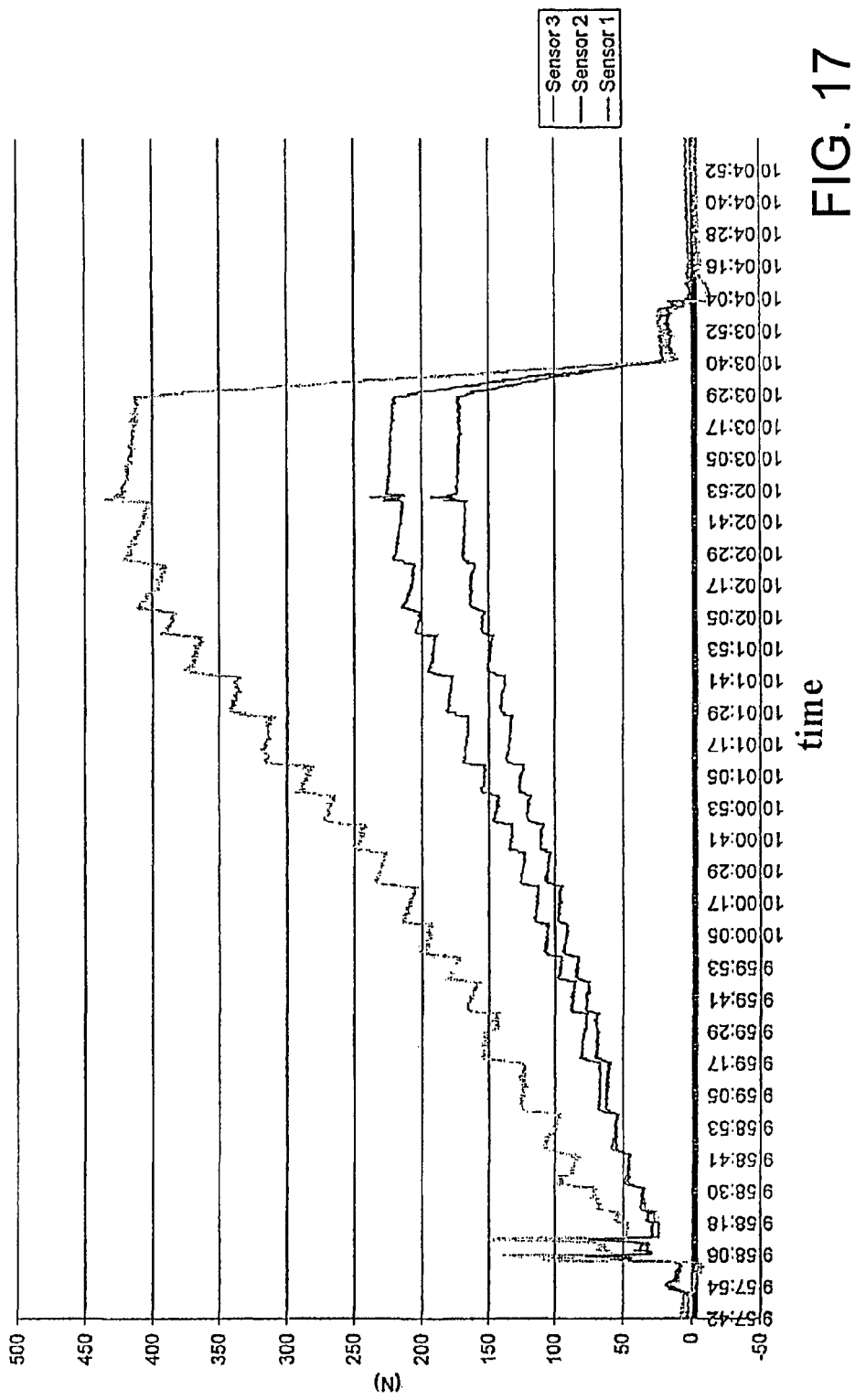

US 8,104,477 B2

RADIOLUCENT FASTENING DEVICES FOR SECURING A PART OF A BODY DURING A MEDICAL PROCEDURE

RELATED APPLICATION DATA

This application claims priority of U.S. Provisional Application No. 60/948,712 filed on Jul. 10, 2007, and EP 07 112127 filed on Jul. 10, 2007, which are incorporated herein by reference in their entirety.

FIELD OF THE INVENTION

The invention relates generally to a fastening device for securing the position of a part of a patient's body, such as a head, during an operation and/or during other medical procedures.

BACKGROUND OF THE INVENTION

Fastening devices for securing the position of a part of a body (for example, a head) during medical procedures are known. Such medical procedures may include operations. The head of a patient should be secured during operations requiring high precision (for example, neurosurgery of the brain wherein a tumor is removed). In such operations, minimal deviations from a planned incision could have extremely negative consequences for the patient, since important portions of the brain could be unintentionally injured and result in impairment of brain function. To minimize this risk, a patient's head is firmly secured during cranial neurosurgery.

In the prior art, head clamps including several fastening devices may be used to secure a patient's head. The prior art head clamps include stirrup-shaped device that further includes protrusions at least three securing points. A fastening device with a tip is situated at each of the three securing points to secure the patient's head to the head clamp. Three-point head clamps and four-point head clamps are common. In the example of a three-point head clamp, one securing point may be situated on one side of the head and the other two securing points may be situated on the other side of the head. In the example of a four-point head clamp, one securing point is situated on each side of the head and two additional securing points support and/or secure the head from below. For head securing, it may not be sufficient to use fastening devices that do not cut through or into the skin and the bone beneath. Ordinarily, such non-invasive securing devices do not have the ability to firmly secure the head. Thus, pins may be used as fastening devices in combination with head clamps. The pins may be small rod-shaped bodies provided with a tip, which are fastened to the head clamp and inserted into the head. The pins may be driven through the scalp into the cranial bone by turning a securing screw.

Conventional pins in accordance with the prior art may be manufactured from a metallic material. Exemplary materials that have been used include high-grade steel and titanium alloys. These materials exhibit a relatively good resistance to mechanical stress.

Resistance to mechanical stress is not, however, the only criterion that should be considered when selecting the material for a fastening device. In general it may be desirable to produce the fastening device from a material that satisfies the following requirements:

1. Resistance to Mechanical Stress

A patient's head should be secured very firmly and very securely. Local mechanical material stresses on the fastening device are extremely high as the mechanical forces for securing the head are focused on a very small region on the tip of the fastening device. The fastening device, therefore, should not deform under large forces. Moreover, the fastening device should not splinter or otherwise divide because fragments could remain lodged in the patient's head after the fastening device has been removed.

2. Ability to be Sterilized

As the fastening device may be used as an invasive medical product, it is desirable for it to be sterilized. Various types of sterilization are possible, including: heat sterilization methods (for example, steam sterilization and hot air sterilization), cold sterilization methods (for example, gas sterilization and sterilization using ionizing radiation), and sterilization using chemical solutions (for example, aldehydes, peracetic acid, halogens, peroxides, etc.). If sterilization by heat is performed, then the material to be sterilized should exhibit a high resistance to heat and have low water absorbability. In the case of chemical sterilization, the material must be chemically inert.

3. Biocompatibility

As the fastening device may pierce both the skin and the bone of a patient, it may be considered an invasive medical device suitable for short-term use (for example, Class IIa in accordance with Appendix IX of council directive 93/42/EEC). Therefore, it is desirable that the material be biocompatible.

4. Absence of Artifacts in Imaging Methods

Operations requiring a very high level of precision often may be accompanied by imaging methods, including intra-operative imaging. Accordingly, a recording may be taken (for example, using a CT scanner or an MRT scanner) during the operation, wherein it is important to achieve high-quality scan recordings. The use of certain fastening device materials may cause distortion or artifacts in the recordings. Metals are generally radio-opaque as well as some ceramics, whereas plastics are generally radiolucent. Accordingly, conventional fastening devices made of high-grade steel and titanium alloys may cause numerous artifacts.

Efforts have been made to manufacture a head clamp pin from sapphire, which is radiolucent. Such a pin, however, may not withstand the mechanical stresses encounter during use and still shows remaining artifacts.

Finally, the shape of the objects also can contribute to artifacts, for example, tips or edges. In practice, it is difficult to predict whether or not a certain fastening device will cause artifacts or predict the artifacts' shape or magnitude.

SUMMARY OF THE INVENTION

A fastening device in accordance with the invention for securing a position of a part of a body, for operations and other medical procedure, includes a holding portion and a penetrating portion connected to the holding portion, wherein the holding portion of the fastening device includes a portion that can be connected to a securing device. The holding portion may be a cylindrical body which, for example in the case of a pin for a head clamp, is inserted into said head clamp at a certain point and firmly screwed into it. The holding portion does not have to be cylindrical; other shapes are acceptable. For example, the holding portion could have a rectangular cross-section, rather than a round cross-section. The penetrating portion connected to the holding portion is a portion that may be tapered towards the point or tip with which the fastening device penetrates into the body. Such a penetrating portion may be conical or non-conical. Both the holding portion and the penetrating portion may be solid, as compared to hollow.

A conventional metal alloy pin shall be discussed as an example and for comparison. The conventional pin may be formed in one piece, wherein its overall shape is composed of a cylindrical shape and a conical shape. In this example, the cylindrical shape forms a holding portion, and the conical portion forms a penetrating portion.

If the holding portion and the penetrating portion are formed in one piece, the holding portion and the penetrating portion may continuously transition into each other, without an abrupt separation between the two portions. The conventional pin is ordinarily held on one side keeping the other side free to penetrate into the body to secure its position. In this respect, the conventional pin includes a holding portion and a penetrating portion.

In an example in accordance with the invention, the fastening device may include unsubstituted, monosubstituted, or multisubstituted polyphenylene (for example, unsubstituted, monosubstituted, or multisubstituted polyparaphenylene). The entire fastening device can be made in one piece of the above-mentioned substances or the fastening device made include at lest two pieces wherein only the penetrating portion is made of the above-mentioned materials. The holding portion can be made of a single part or can be made of a number of parts. The holding portion also can consist entirely or partly of the aforementioned materials.

In an example in accordance with the invention, the polyphenylene comprises polyparaphenylene. The structure of polyparaphenylene is a linear chain that imbues the substance with a particularly high stability. It is also possible, however, to provide a polyphenylene in which the monomeric phenyl units are linked once, more than once, or throughout in the meta and/or ortho position.

The polyphenylenes (for example, the polyparaphenylenes) can be monosubstituted or multisubstituted by the following: $C_1$-$C_8$ alkyls (for example, methyl, ethyl, propyl, butyl, pentyl, hexyl, heptyl and/or octyl groups). The $C_1$-$C_8$ alkyl substituents can be linear or branched. Thus, isopropyl, sec-butyl, tert-butyl substituents and any isomers of the $C_5$-$C_8$ alkyl substituents may be used. The substituents also can be $C_2$-$C_8$ alkenyls (for example, linearly linked or branched-linked ethenyl, propenyl, butenyl, pentenyl, hexenyl, heptenyl and/or octenyl groups). The substituents also can be linearly linked or branched-linked $C_2$-$C_8$ alkinyl groups (for example, ethinyl, propinyl, butinyl, pentinyl, hexinyl, heptinyl and/or octinyl groups, which are each linearly linked or branched-linked). The substituents also can be $C_1$-$C_8$ alkoxyls (for example, methoxy, ethoxy, propoxy, butoxy, pentoxy, hexoxy, heptoxy and/or octoxy groups). Alkenyl and/or alkinyl substituents and alkoxyl substituents, can replaced by any isomeric forms. The substituents also can be cyclic, non-aromatic, or aromatic $C_4$-$C_8$ alkyl substituents (for example, cyclobutyl, cyclopentyl, cyclohexyl, cycloheptyl or cyclooctyl radicals).

In an example in accordance with the invention, one or more substituents of the polyphenylenes (for example, the polyparaphenylenes) can be selected from the main group of halogens (for example, chlorine, iodine and/or bromine). The substituents also can consist of and/or comprise a nitro group, a hydroxyl group and/or an amino group.

In an example in accordance with the invention, the polyphenylenes (for example, the polyparaphenylenes) can be monosubstituted or multisubstituted by a phenyl, benzyl or the benzoyl group. In the case of substituting for polyparaphenylene, the phenyl, benzyl or the benzoyl group can be situated in the ortho and/or meta position.

The substituents mentioned herein are indicated in FIG. 1, as examples R and R' (described in greater detail below).

All the aforesaid unsubstituted, monosubstituted or multisubstituted polyphenylenes (for example, all the aforementioned unsubstituted, monosubstituted, or multisubstituted polyparaphenylenes) may be fiber-reinforced.

In an example in accordance with the invention, the material of the fastening device can comprise unsubstituted, monosubstituted, or multisubstituted polyphenylene copolymers (for example, unsubstituted, monosubstituted, or multisubstituted polyparaphenylene copolymers). The substituents mentioned above may respectively be considered as substituents.

The aforesaid copolymers can be statistical copolymers in which the distribution of at least two different monomers in the chain is random. The copolymers can be gradient copolymers in which the proportion of a monomer as compared to at least one other proportion of the monomer changes in the course of the chain. The copolymer can be an alternating copolymer comprising a regular arrangement of at least two different monomers along the chain. The copolymers also can be block copolymers which consist of at least two long sequences or blocks of each monomer. Depending on the number of blocks, these copolymers also are said to be bi-block copolymers, tri-block copolymers, etc. Additionally, the copolymers can be so-called graft copolymers, in which the blocks of a monomer are grafted onto the frame of another monomer.

In an example in accordance with the invention, the fastening device may include a polyparaphenylene copolymer, wherein the first monomer is monosubstituted in the ortho position, the second monomer is monosubstituted in the meta position, and the substituent in each case is a benzoyl group (—CO—$C_6H_5$), wherein the first monomer and the second monomer may be arranged alternately. It is, however, possible for the polyparaphenylene copolymer to be a statistical copolymer, a gradient copolymer, a block copolymer, or a graft copolymer.

In an example in accordance with the invention, the fastening device includes a silicon nitride ceramic (for example, a β silicon nitride ceramic). This ceramic can be a pure silicon nitride ceramic. Other ceramics also may be mixed into or added to the silicon nitride ceramic. The silicon nitride ceramic also may be a fiber-reinforced silicon nitride ceramic. Resistance to cracking can be increased by using long fibers to reinforce the ceramic. The addition of long fibers also can improve other properties (for example, tensile strength, fracture toughness and resistance to thermal shock). The improved properties generally enable a broader scope of applications for silicon nitride ceramics and technical ceramics.

In an example in accordance with the invention, the penetrating portion and/or the holding portion of the fastening device may be aligned in the same longitudinal axis and be axially rotationally symmetrical. The holding portion may be cylindrical while the penetrating portion may be conical. The penetrating portion may include a cylindrical portion, a non-conical portion, and/or a conical portion, wherein the different geometric shapes may transition into each other. The penetrating portion may be formed in one piece or may be formed of multiple pieces.

In one example in accordance with the invention, the penetrating portion includes a tip, and the penetrating portion does not have the shape of a cone. The penetrating portion may be tapered towards a point that penetrates into the body to be secured. In this respect, the tip can be almost ideally pointed, however, it is possible for the tip to have a measurable diameter that is less than or equal to about 0.5 mm (for example, 0.5 mm, 0.2 mm, 0.1 mm). As a practical matter, the tip should be sharp enough to penetrate into the body to be secured without issue.

In accordance with the invention, the penetrating portion does not have to be conical. Other shapes of the penetrating portion (when considering the penetrating portion as a whole) may be acceptable. As mentioned above, the tip of the penetrating portion may have a measurable diameter. For example, a first region of the penetrating portion may be formed in the shape of a cone, but is connected to another region of the penetrating portion that is not conical. The second region of the penetrating portion can, for example, be ogival in shape. The second region may be a concave or convex portion that is connected to the conical portion and the conical portion includes a tip.

In an exemplary fastening device in accordance with the invention, the penetrating portion may comprise a first region in the form of a non-conical truncated cone that borders the holding portion. A second region in the form of a cone may form the tip, wherein the angle of the surface of the truncated cone with respect to the axis of the truncated cone differs from the angle of the surface of the cone with respect to the axis of the cone.

In an example in accordance with the invention, the penetrating portion as a whole may include a cone and a truncated cone, wherein the penetrating portion is formed in one piece. In this example, the angle of the outer surface of the cone with respect to the axis of the cone may be greater than the angle of the outer surface of the truncated cone with respect to the axis of the truncated cone. The truncated cone may border and/or be connected to the holding portion. Additionally, the penetrating portion may include a number of consecutive truncated cones and a cone that forms the tip. The penetrating portion may be formed in one piece, multiple pieces, or may be formed in one piece with the holding portion.

In an example in accordance with the invention, the diameter of the fastening device, as measured orthogonally with respect to the rotational axis, may monotonically increase from the tip of the penetrating portion to the end of the holding portion that extends away from the penetrating portion. The diameter of this exemplary fastening device, as measured in a direction which is orthogonal with respect to the axis, should monotonically increase, starting from the end which is designed to penetrate into a body to the end which is connected to the holding portion.

In an example in accordance with the invention, the penetrating portion may be formed in two pieces, wherein a first piece is in firm contact with a second piece, and wherein the first piece includes a tip. The term "in two pieces" herein is understood to mean the presence of two separate work pieces that can be brought into firm contact with each other.

Firm contact in this context means that the contact is firm enough so that the penetrating portion is not dismantled into its two component parts when it is fastened for the purpose of securing the position of a body and when it is removed again. The firm contact can be generated by pressure, adhesion, or other acceptable method. The two-piece example has the advantage of selecting different materials for each piece of the penetrating portion. One piece of the penetrating portion can be selected for its specific location of use (for example, its position within the penetrating portion and the associated function). In this manner, the tip material may be selected to be mechanically stable and firm, whereas the remainder of the penetrating portion may be formed of a material that may be less firm, but may be more radiolucent.

In an example in accordance with the invention, one piece of the penetrating portion includes a tip made of ceramics (for example, a silicon nitride ceramic). A second piece of the penetrating portion may be made of unsubstituted, monosubstituted, or multisubstituted polyphenylene (for example, unsubstituted, monosubstituted, or multisubstituted polyparaphenylene). The second piece may be made of a polyparaphenylene copolymer or a substituent. All the configurations and substituents mentined in this Summary may be suitable. The substituents noted above apply to the polyphenylenes, polyparaphenylenes, and polyparaphenylene copolymers.

The unsubstituted, monosubstituted, or multisubstituted polyphenylenes described above (for example, unsubstituted, monosubstituted, or multisubstituted polyparaphenylenes, and polyparaphenylene copolymers) have good material properties with respect to radiolucency, resistance to mechanical stress/hardness, biocompatibility, and the ability to be sterilized. Such materials are proven as good options for the manufacture of other objects used in the field of implant medicine. Such other objects include screws, implants, osteosynthesis plates, nails, etc. Instruments produced from the described unsubstituted, monosubstituted or multisubstituted, polyparaphenylenes are radiolucent and can remain in the patient's body during intra-operative CT scans or MRT scans. Examples of these instruments include tenacula, retractors, spreaders, tweezers, clamps, securing forceps, and stackers for clip suture apparatus.

BRIEF DESCRIPTION OF THE DRAWINGS

The forgoing and other features of the invention are hereinafter discussed with reference to the figures.

FIGS. 6A to 6H show exemplary test results of axial forces plotted against time for exemplary pins in accordance with the invention made of different materials using the experimental design of FIG. 4.

FIGS. 7A to 7F show exemplary pins in accordance with the invention made of different materials, after they have been used in a head clamp.

FIGS. 17 and 18 show exemplary test results of axial forces plotted against time for exemplary pins in accordance with the invention made of different materials using the experimental design of FIG. 4.

DETAILED DESCRIPTION

Figure 1A:
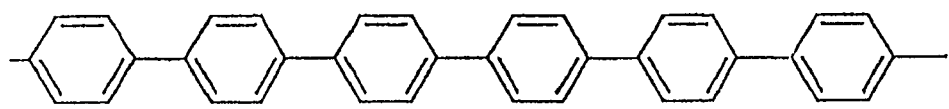
FIGS. 1A to 1D show various ways in which a polyphenylene can be configured.

The materials identified in the Summary of the Invention were tested to develop a fastening device that optimizes the aforementioned performance criteria including: resistance to mechanical stress, ability to be sterilized, biocompatibility, and prevention of artifacts in medical imaging. The test materials were selected from a group of ceramics and a group of polymers and include the following materials:

Ceramics:
machinable glass ceramic sold under the registered trademark MACOR® of Corning Inc. Corp. of New York, USA
silicon nitride sold under the tradename SNI 750 of Ceratec GmbH of the Fed. Rep. of Germany
$ZrO_2$ (zirconium oxide)

Polymers:
self-reinforcing polyparaphenylene copolymer with benzoyl substituents sold under the registered trademark TECAMAX® SRP of Ensinger GmbH of the Fed. Rep. of Germany
polyether ether ketone sold under the registered trademark TECAPEEK® classix of Ensinger GmbH of the Fed. Rep. of Germany
polyether ether ketone with 30% carbon fibers sold under the registered trademark TECAPEEK® CF30 of Ensinger GmbH of the Fed. Rep. of Germany
polyether ether ketone with 30% glass fibers sold under the registered trademark TECAPEEK® GF30 of Ensinger GmbH of the Fed. Rep. of Germany

Biocompatibility

The materials were acknowledged compatible or tested for biocompatibility in accordance with methods well known in the art.

MACOR is known in the art to be biocompatible and is used in ear, nose and throat (ENT) medicine as an auditory ossicle implant.

SNI 750 samples were subjected to in-vitro tests, and through these tests it was determined that silicon nitride exhibits a bio-inert behavior. It is noted that the SNI 750 material of "Ceratec GmbH" used in the tests does not presently have biocompatibility certification.

Zirconium oxide material is presently used in implantation operations (for example, for hip implants). Through comprehensive in-vitro and in-vivo tests, it was shown that zirconium oxide exhibits a bio-inert behavior.

TECAMAX SRP material of the company "Ensinger GmbH" is certified as being biocompatible.

Through investigations conducted in osteoblast cultures, it was determined that TECAPEEK classix does not show any cytotoxic behavior. Cylindrical samples of PEEK were accepted in the muscular tissue of mice, even after an implantation period of 12 weeks.

TECAPEEK CF30 and TECAPEEK GF30 are fiber-reinforced polymers that are known to have a lower chemical resistance and a tendency to form arrangements of particles and, thus, pose a biocompatibility risk.

Sterilization

Ethylene oxide sterilization can be used for all the materials investigated herein.

Resistance to Mechanical Stress

Various tests were conducted to investigate the resistance to mechanical stress of the material and its suitability for securing a body during operations. These tests include measuring forces acting on the respective pin using various sensors when the pins were used to secure a head. The investigation included observation of the penetration depth of conventionally available pins into a patient's head. Pins made of the subject materials were tested to determine whether they have deformations or defects after they have been used to secure the position the head.

Three-dimensional CT scans were taken to investigate the creation and/or absence of artifacts in imaging recordings, wherein pins manufactured from the different materials were fastened to a special head model filled with a wax gel that simulates the human brain.

Figure 1B:
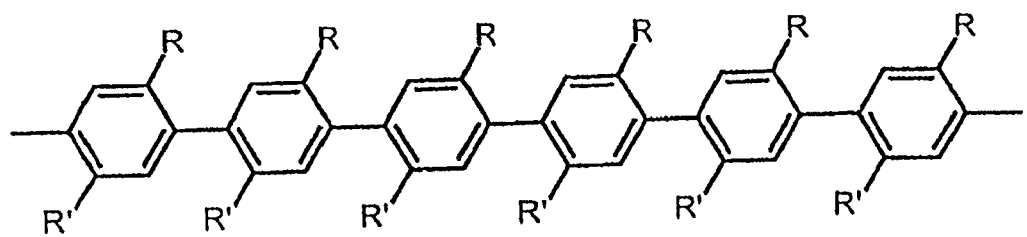
Figure 1C:
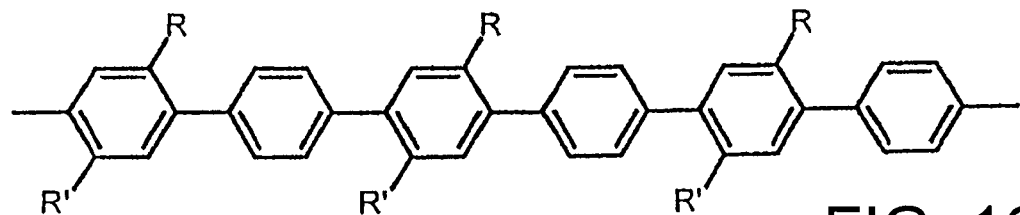
Figure 1D:
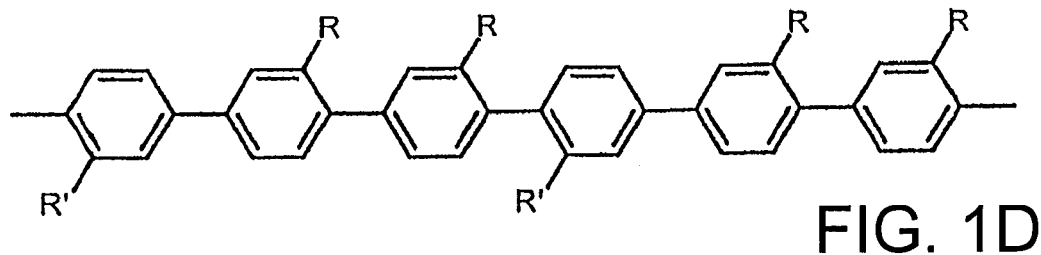

FIGS. 1A through 1D show various ways in which a polyphenylene can be configured. FIG. 1A shows a section from an unsubstituted chain of polyparaphenylene. The linear structure of the chain, which is mainly responsible for the high stability of polyparaphenylene, can be seen. FIG. 1B shows a section from a chain of multisubstituted polyparaphenylene. Each phenyl unit may multisubstituted. The substituents are indicated by R and R' respectively, wherein R and R' can be identical or different. In the example of FIG. 1B, the substituents are arranged opposite each other in the para position (i.e., they are each situated in the 2,5 position with respect to the chain of phenyl units). FIG. 1C shows another section from a chain of polyparaphenylene in which the individual phenyl units are alternately unsubstituted and multisubstituted (in this example, bisubstituted). FIG. 1D shows another example of a section of a chain of a polyparaphenylene, wherein each individual phenyl unit is monosubstituted. The substituents may be situated either in the ortho position or in the meta position. In accordance with the example shown, a substituent R' is situated in the ortho position, whereas a substituent R is situated in the meta position. The substituents R and R' can be different or identical. The substituents R and R' can be any of the substituents explicitly mentioned above.

Figure 2:
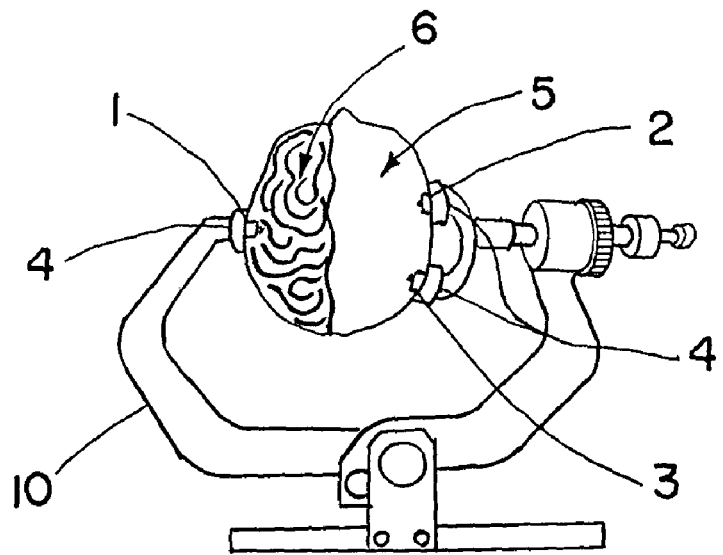
FIG. 2 shows an example of securing a skull using a head clamp that includes pins.
Figure 3:
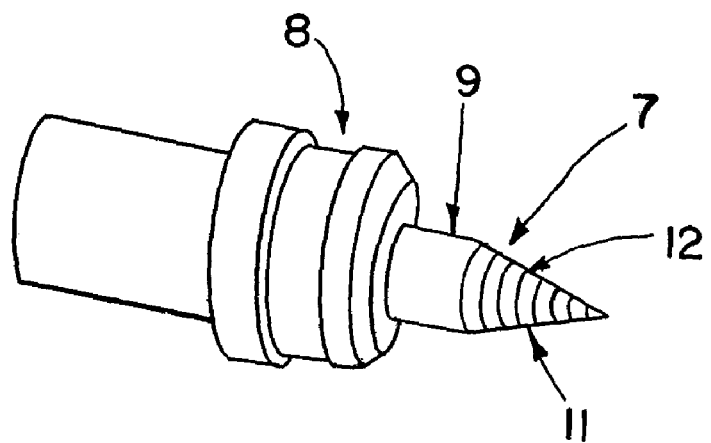
FIG. 3 shows an exemplary pin including marking rings for measuring depth.

FIG. 2 shows a Mayfield type head clamp 10 as is known in the prior art. The head is secured at three points by pins 1, 2, 3. Pins 1, 2, 3 are secured in framing elements 4. Pin 1 may be situated centrally on the left-hand side of a head 5, whereas pin 2 and pin 3 may be situated on the other side of the head 5. Also shown in FIG. 2 is brain 6. Head clamps of this type typically have three points (as shown) or four points FIG. 3 shows an exemplary pin 7 that can be used in connection with the head clamp 10 shown in FIG. 2. In this example, the pin 7 is manufactured from high-grade steel as is known in the prior art. The pin 7 is firmly connected to a holding device 8. The pin includes a holding portion 9 that is connected to the holding device 8, and a penetrating portion 11. The penetrating portion 11 may be conical and may be marked with rings 12. The marking rings 12 allow the surgeon to measure the penetration depth of pin 7 when pin 7 is used to secure the head 5. The pin 7 shown, provided with marking rings 12, is a pin made of high-grade steel.

Figure 4:
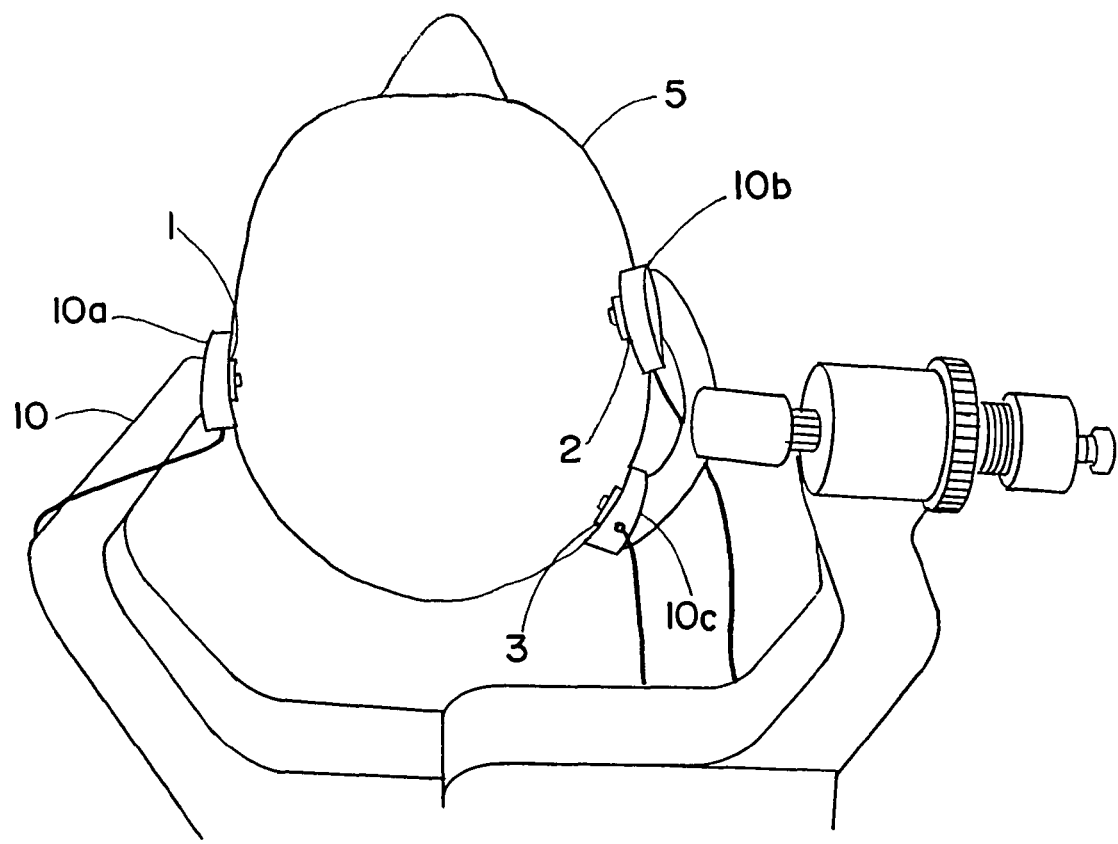
FIG. 4 schematically shows an experimental design for measuring the forces acting on the pins.

FIG. 4 schematically shows an experimental arrangement used to measure the forces acting on the pins. The three-point head clamp 10 is shown framing a head 5 and securing the head 5 at three points by three pins 1, 2, 3. In this experimental arrangement, sensors 10a, 10b and 10c are situated at the pins 1, 2, 3 and respectively measure the forces acting on the pins 1, 2, 3 and provide the data to a data evaluating unit (not shown).

First Series of Experiments

Figure 5:
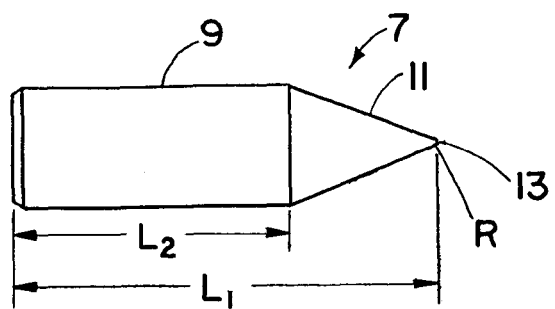
FIG. 5 is a schematic representation of an exemplary pin.
Figure 6A:
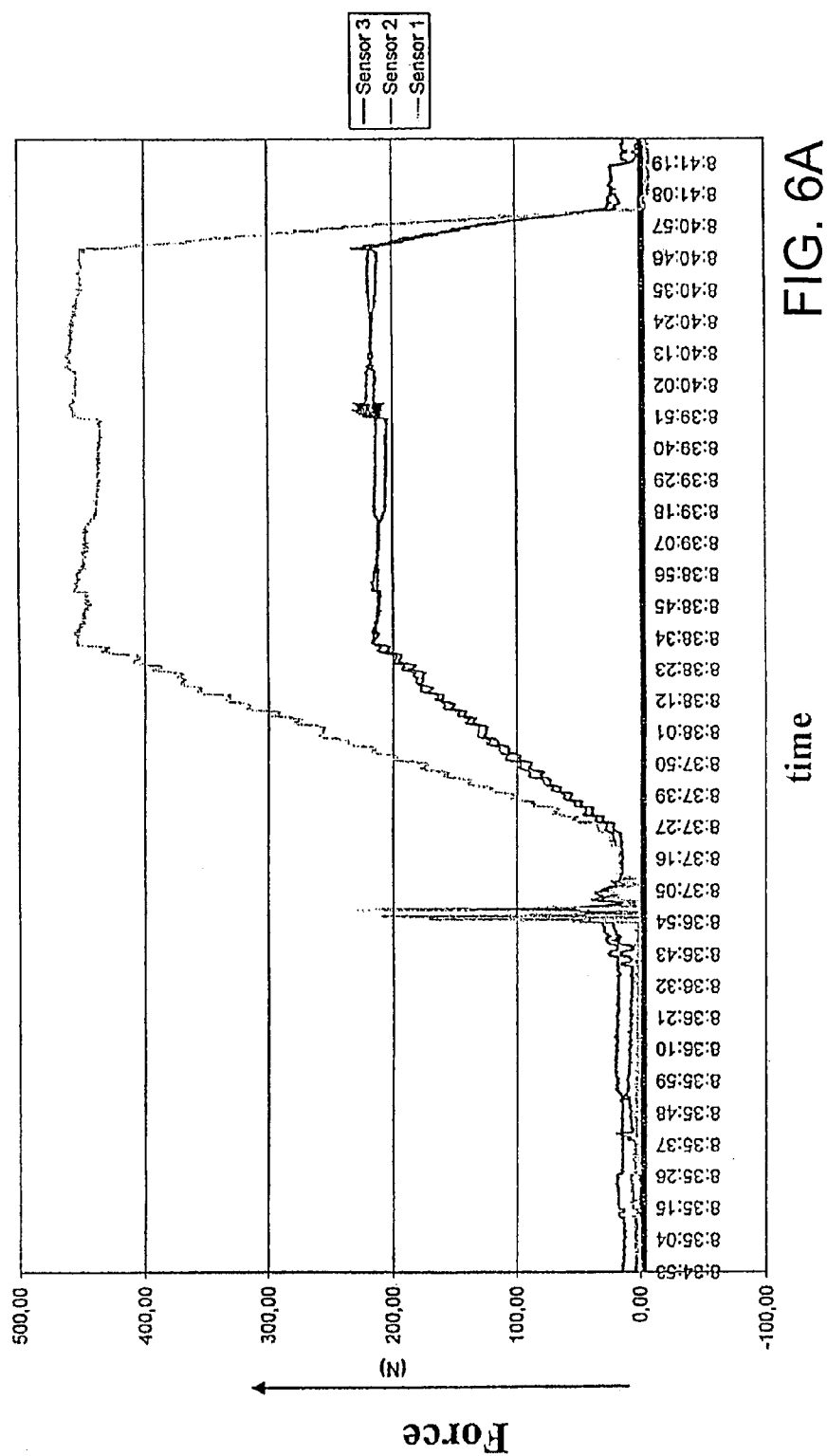
Figure 6B:
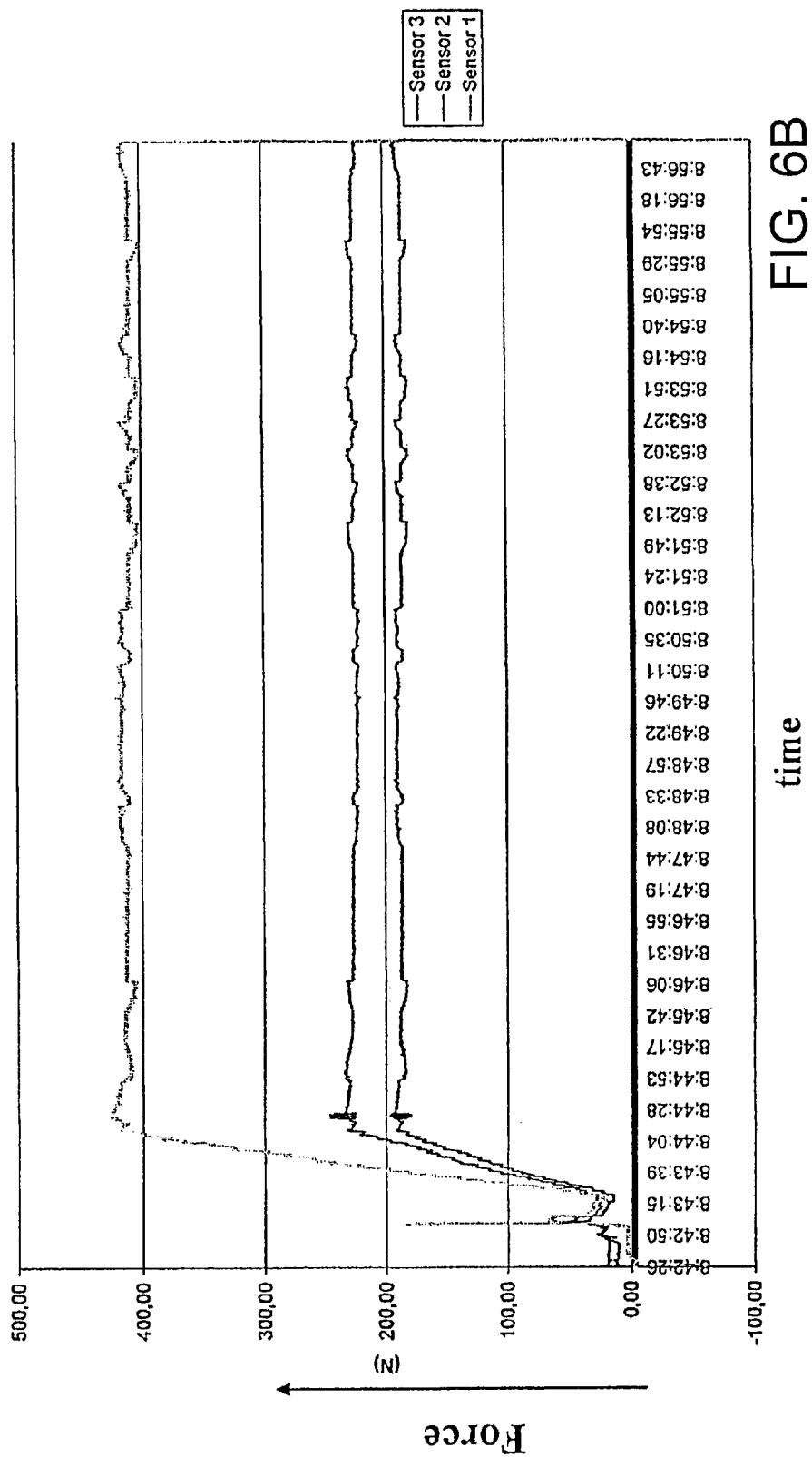
Figure 6E:
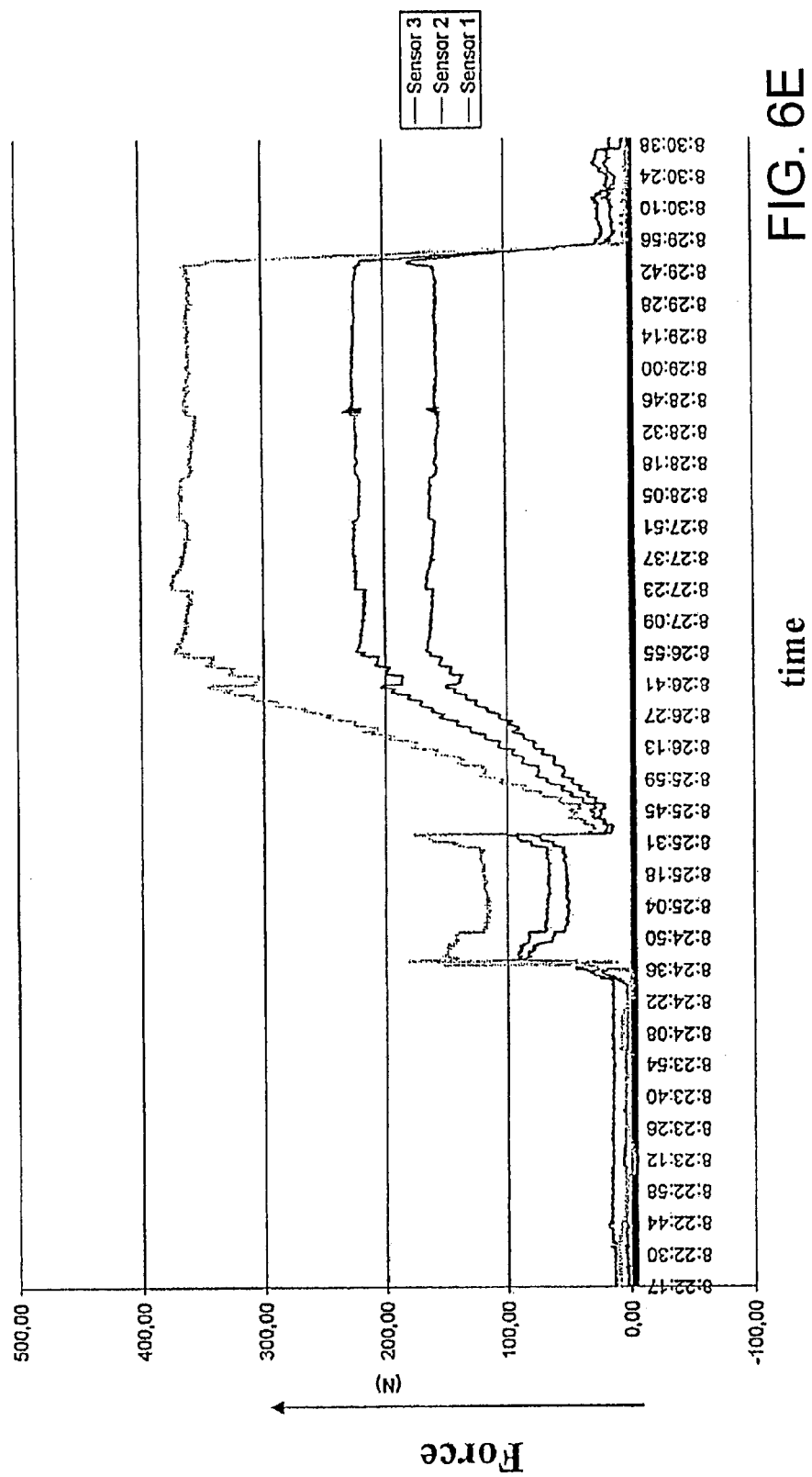
Figure 6G:
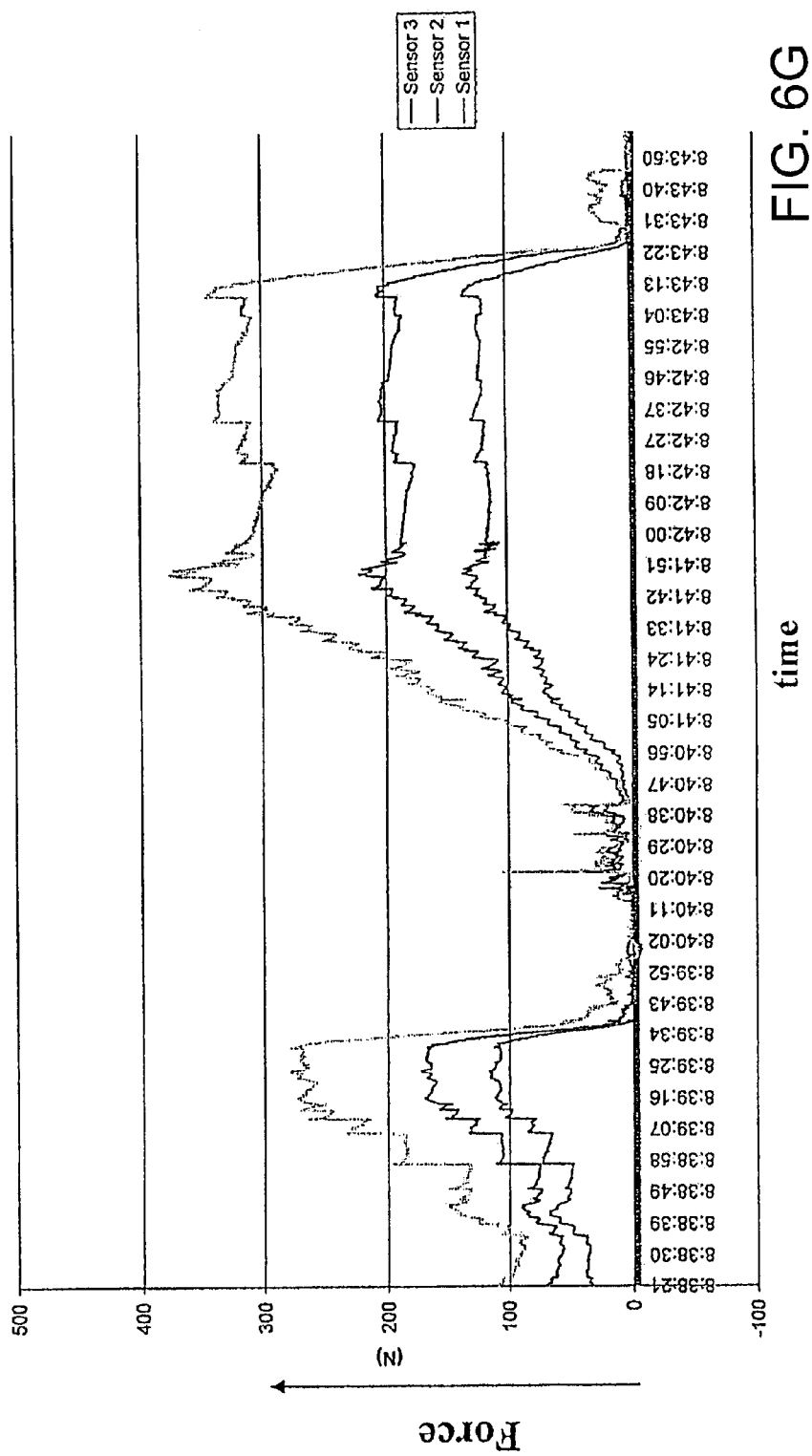
Figure 6H:
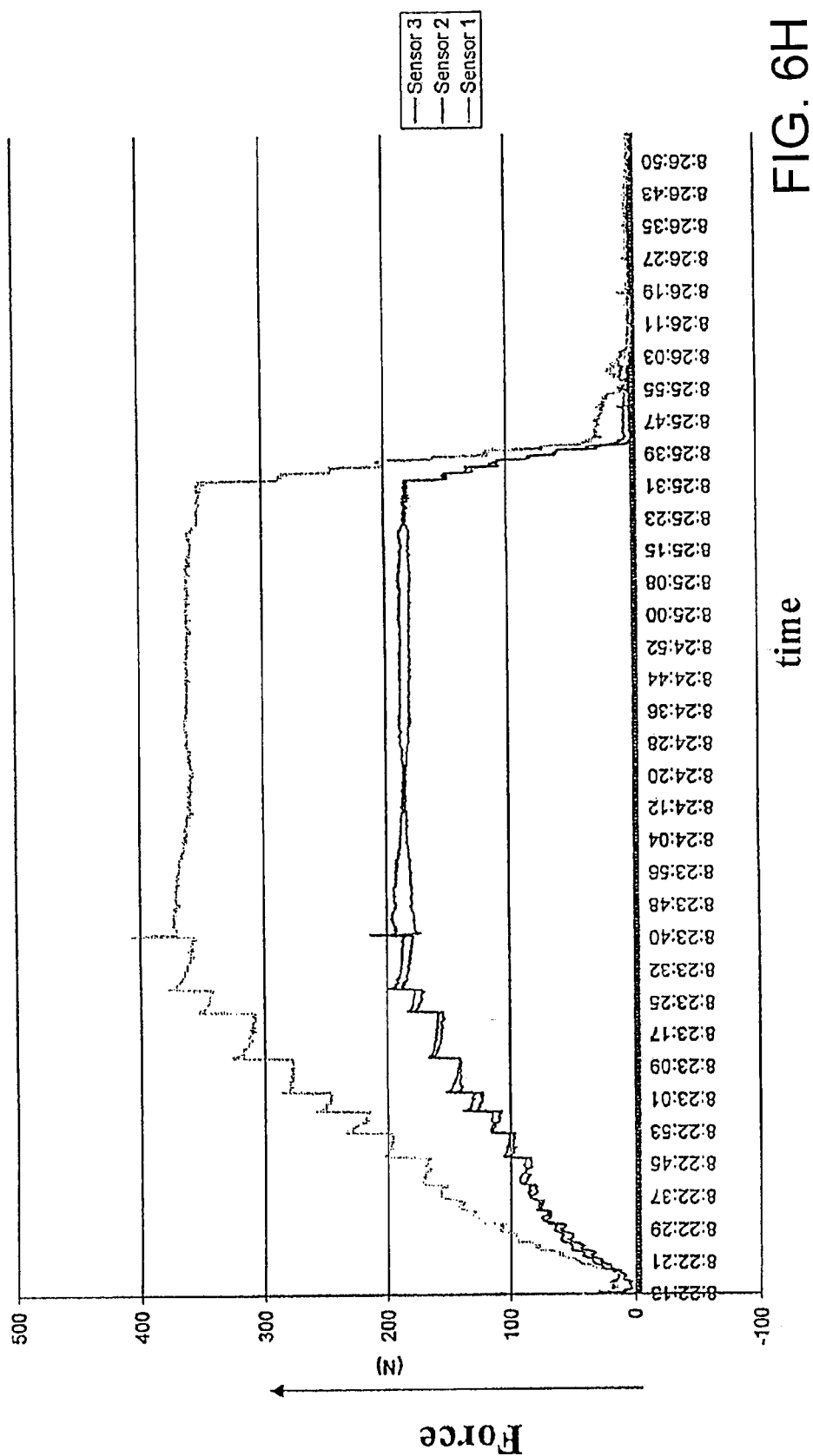

FIG. 5 is a sectional drawing along an axis of a pin 7 and schematically shows the geometry of the pin 7, such as was used in a first series of experiments. The pin 7 is formed in one piece and includes a holding portion 9 and a penetrating portion 11. The holding portion 9 may be cylindrical, and the penetrating portion 11 is formed to be conical. The penetrating portion 11 is connected to the holding portion 9 and comprises a tip 13. The tip 13 may have a measurable diameter and, thus, may not be a perfect point. In the example, the radius of the tip 13 is 0.1 mm. Also shown in FIG. 5, are the dimensions of the exemplary pin 7. The overall axial length of the pin 7 is 20 mm, wherein 13 mm of this length is allotted to the holding portion 9. The holding portion 9 is longer than the penetrating portion 11, however this is not necessary, but rather may depend on the way in which the holding portion is to be fastened to a suitable holding device (for example, a head clamp). The dimensions shown in FIG. 5 are thus not limiting, but are rather to be understood as exemplary.

In the first series of measurements, the penetration depths of the pins 1, 2 and 3, into the head 5 were measured. These measurements were conducted within the framework of securing the position of the head, using the pins 7 as shown in FIG. 3. To this end, the number of rings 12 that penetrated into the head and could no longer been seen after the head was secured were recorded. Through these tests, it was shown that the penetration depth of pin 1, as shown in FIG. 2, was different to the penetration depths of pins 2 and 3, as shown in FIG. 2. This is a logical consequence of the fact that a single pin (pin 1) is used on one side of the head shown as a model in FIG. 2, while the forces acting on the other side are distributed over the pins 2 and 3. The following depth data was recorded:

Pin 1: penetration depth<1.5 mm (axial force≈360 N)
Pin 2: penetration depth≦1.0 mm (axial force≈250 N)
Pin 3: penetration depth<1.0 mm (axial force≈180 N).

Once the penetration depth had been measured using the pin 7 that is characterized by rings 12, pins made of different materials were prepared for a first series of tests. These materials were MACOR, SNI 750, TECAMAX SRP, TECAPEEK classix, TECAPEEK $CF_{30}$, and TECAPEEK GF30. Three series of experiments were conducted on each of ten cadavers in a pathology institute, wherein the heads of the cadavers were secured by neurosurgeons in a manner consistent with surgical conditions. The head of the corpse was first secured and was then moved to test the securement, and the head clamp was loosened to release the head. The pins, once removed from the head clamp, were examined.

During the test, the forces acting on the pins 1, 2, 3 were measured using sensors 10a, 10b, 10c and are plotted against time. By way of example, one diagram is respectively attached as FIGS. 6A through 6H for each pin material used.

The acting forces move within a certain range, irrespective of the pin material used. The maximum forces acting on pin 1 are in a range around 400 N. There are fluctuations, however, around this maximum value and in some cases the maximum values were approximately 450 N when the test subject was completely secured (see FIG. 6A, steel pin). In another example, the maximum forces acting on pin 1 were slightly below 400 N, at approximately 380 N (see FIG. 6E, TECAMAX SRP).

The maximum forces acting on pins 2 and 3 were significantly lower as pins 2 and 3 were situated on the same side of the head clamp and therefore the load was distributed between the two pins. The maximum forces for pins 2 and 3 were within a range around 200 N. The maximum force acting on pin 3 tended to be slightly lower than the maximum force acting on pin 2.

The force curves for the different pins are common in that the measured force increased during the securing process, approximately linearly aside from individual micro-fluctuations. A level region of the graphs follows the increasing region. FIG. 7 shows, by way of example, the three pins of each measuring process, each showing the pins 1, 2, 3 after they have been tested in a head clamp. The pins illustrated were made from the following materials:

A: MACOR
B: TECAPEEK classix
C: SNI 750
D: TECAPEEK CF30
E: TECAMAX SRP
F: TECAPEEK GF30

The pins were visually examined using a surgical microscope and any deformations and/or defects (for example, cracks or splintering) caused by the test were observed and recorded. Some deformation and/or defects were noted in each group of pins comprising a certain material, however, the defects had varying degrees. For example, FIG. 7 shows that the tip of a pin may be missing after the pin has been used. The pins often exhibited deformations (particularly in the region of the tip) wherein the deformations were particularly pronounced in the examples of materials TECAPEEK classix, TECAPEEK CF30, and TECAPEEK GF30. Based on the visual examination, the pins made of the materials TECAMAX SRP and SNI 750 yielded the best results (see FIGS. 7E and 7C). The TECAMAX SRP and SNI 750 pins nearly maintained their initial symmetrical shape after having been used. Pins situated at the pin 1 location (that was exposed to the greatest loading) were the only pins of these materials that showed any signs of deformation and/or defects. The tips of these pins were damaged but otherwise the pins remained largely intact.

The results of the mechanical load test are summarized below in Table 1:

TABLE 1

| Material | Deformations | Defects |
| --- | --- | --- |
| MACOR | − | − |
| SNI 750 | + | − |
| TECAMAX SRP | + | − |
| TECAPEEK classix | − | − |
| TECAPEEK CF30 | − | − |
| TECAPEEK GF30 | − | − |

In interpreting the tables printed herein, please refer to the following nomenclature:

"++" indicates that an excellent result was observed
"+" indicates that a suitable result was observed
"0" indicates that a satisfactory result was observed "−" indicates that a negative suitability of the pins was observed.

This nomenclature also applies to all of the tables herein. Applying the above to Table 1, it is noted that SNI 750 and TECAMAX SRP exhibited the smallest deformation.

Figure 8A:
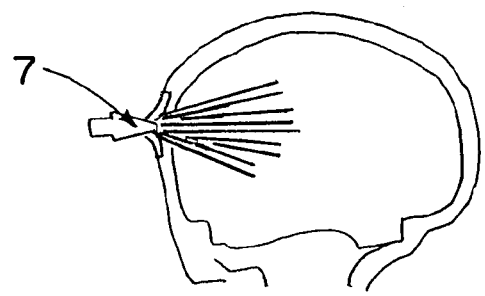
FIGS. 8A to 8D show exemplary x-ray tomograms of a cranial phantom filled with gel, wherein pins in accordance with the invention made of different materials are secured to the skull.
Figure 8B:
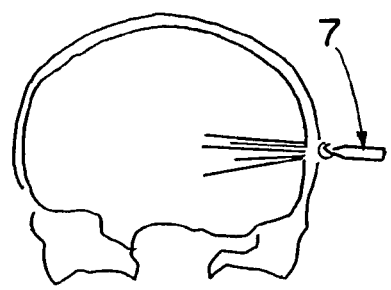
Figure 8C:
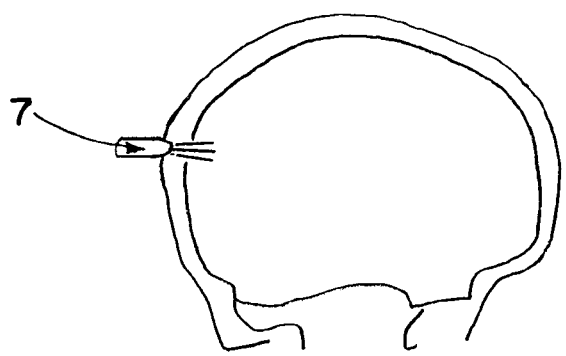
Figure 8D:
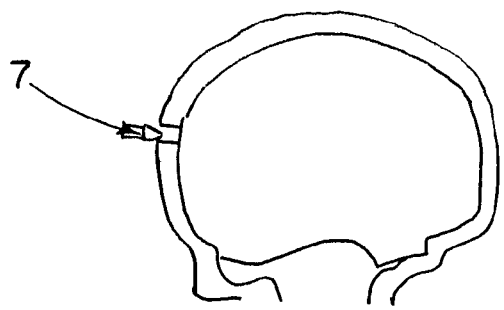

In a subsequent series of tests, the two most promising candidates from the mechanical stress test, SNI 750 and TECAMAX SRP, were tested with regard to their radiolucency and tendency to create artifacts in medical images. To this end, exemplary pins were fastened to a model that simulates the human brain (for example, a special model filled with wax gel) and various three-dimensional CT scans were taken using pins of different materials. In addition to the two noted candidates, SNI 750 and TECAMAX SRP, pins made of a titanium alloy and of zirconium oxide were used for a baseline comparison. Examples of these CT scans are shown in FIGS. 8A to 8D (FIG. 8A shows a scan using a titanium alloy pin; FIG. 8B—using a zirconium oxide pin; FIG. 8C—using a SNI 750 pin; and FIG. 8D—using a TECAMAX SRP pin). The pins can be seen as a white region in each of the scan recordings. When the pins cause artifacts, black lines are emitted from the pins 7, in many cases in a fanned shape. The artifacts are the black lines, which impede a proper reading or analysis of the recording. In reviewing scan FIGS. 8A through 8D, the greatest formation of artifacts is associated with the conventionally used titanium pins (FIG. 8A). In FIG. 8A, a region near the tip of the pin is completely "blacked" by the formation of artifacts and renders the region unreadable. Major artifacts also occur in the region of the pin when using a zirconium oxide pin (FIG. 8B), but these artifacts are more focused and not as pronounced as the titanium artifacts. Turning to FIG. 8C, the SNI 750 pin yields a significantly better result than when using titanium or zirconium oxide. Using SNI 750, some artifacts are formed in the region of the pin, but the formation is substantially less pronounced than the baseline pins above. The best result was observed when using TECAMAX SRP pins (FIG. 8D). The recordings obtained in this case are almost completely free of artifacts.

The results obtained from the scan recordings with regard to artifact creation are summarized in Table 2:

TABLE 2

| Material | Artifact creation |
| --- | --- |
| Titanium | − |
| ZrO$_2$ | − |
| SNI 750 | 0 |
| TECAMAX SRP | ++ |

As indicated above, use of SNI 750 pins yields satisfactory results and the use of TECAMAX SRP pins yields excellent results.

The results of the first series of experiments are shown summarized below in Table 3. As shown in the Legend, the columns indicate the relevant property and the rows indicate the pin material. It is noted that all test pins have the geometry of pin 7 in FIG. 5.

TABLE 3

| Material | 1 | 2 | 3 | 4 | Ranking |
| --- | --- | --- | --- | --- | --- |
| MACOR | + | + | − | n/a | 7$^{th}$ |
| SNI 750 | + | + | 0 | 0 | 2$^{nd}$ |
| ZrO$_2$ | + | + | 0 | − | 3$^{rd}$ |
| TECAMAX SRP | + | + | 0 | ++ | 1$^{st}$ |
| TECAPEEK classix | + | + | − | n/a | 4$^{th}$ |

TABLE 3-continued

| Material | 1 | 2 | 3 | 4 | Ranking |
| --- | --- | --- | --- | --- | --- |
| TECAPEEK CF30 | 0 | + | − | n/a | 5$^{th}$ |
| TECAPEEK GF30 | 0 | + | − | n/a | 6$^{th}$ |

Legend
1 = biocompatibility,
2 = ability to be sterilized,
3 = resistance to mechanical stress,
4 = artifact creation Also noted here is that artifact creation was investigated only for those materials for which the other three criteria indicated that a material may be suitable as a fastening device in accordance with the invention. If a certain property was not investigated for a fastening device made of a certain material, this is indicated as "not applicable" in Table 3 by the combination of letters "n/a".

Based on the results of the first series of experiments, TECAMAX SRP exhibits the best combination of properties. TECAMAX SRP is biocompatible and sterilizable. TECAMAX SRP performed satisfactorily in the mechanical stress tests and exhibited the best results as compared to all the other substances with regard to artifact creation.

Pins made from SNI 750, yielded the second best combination of properties. The SNI 750 pins fulfill the requirements of biocompatibility, ability to be sterilized, and resistance to mechanical stress, and further provide satisfactory results with regard to artifact creation.

The pins made of zirconium oxide come in third place in the preferred ranking. They are biocompatible, sterilizable, and provide satisfactory results with regard to resistance to mechanical stress. On the negative side, pins made from zirconium oxide produced distorting artifacts in the CT scans.

The materials TECAPEEK classix, TECAPEEK CF30, and TECAPEEK GF30, and MACOR exhibited deficiencies in their resistance to mechanical stress and are regarded as unsuitable candidates for a fastening device in accordance with the invention.

Second Series of Experiments

Following the first series of tests, a second series of tests was conducted to further investigate the two preferred materials TECAMAX SRP and SNI 750 and to further improve the properties of the pins produced from them. In particular, experiments were conducted to improve the pins' resistance to mechanical stress. To this end, the geometry of the pins was altered, and a number of prototypes were manufactured.

Figure 9A:
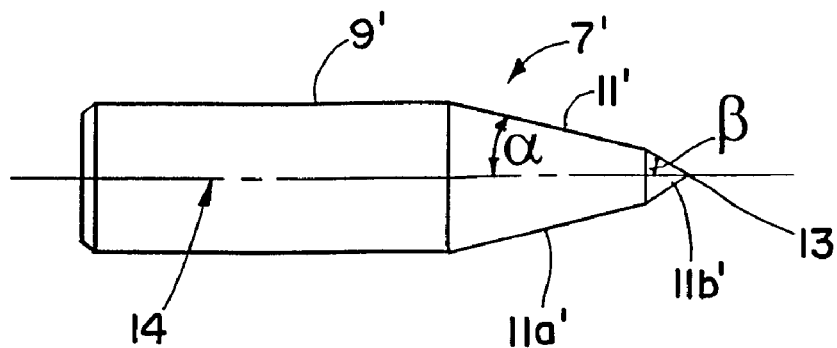
FIG. 9A schematically shows the geometry of an exemplary pin in accordance with the invention.
Figure 9B:
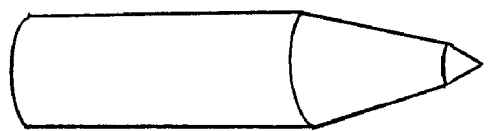
FIGS. 9B and 9C show illustrations of pins corresponding to FIG. 9A of different materials.
Figure 9C:

FIG. 9A shows a schematic drawing of a pin 7' exhibiting an altered geometry; FIGS. 9B and 9C show illustrations of a TECAMAX SRP pin and an SNI 750 pin exhibiting the geometry shown in FIG. 9A.

The pin 7' shown in FIG. 9A comprises a holding portion 9' and a penetrating portion 11', wherein the penetrating portion 11' comprises a tip 13 and wherein the penetrating portion 11' as a whole has a non-conical shape. Instead of a conical shape, the penetrating region 11' is divided into two regions 11a' and 11b'. 11a' is a region of the penetrating portion that on one side borders the holding portion 9'. It is formed in the shape of a truncated cone. The second region 11b' borders the sectional face of the truncated cone that lies opposite the holding portion 9'. It is conical and comprises a tip 13. The pin 7' as a whole comprises a longitudinal axis 14, about which the pin 7' is formed to be axially rotationally symmetrical. An outer surface of the truncated conical region 11a' forms an angle α with respect to the rotational axis 14. An outer surface of the cone of the conical region 11b' forms an angle β with respect to the rotational axis 14. The respective outer surfaces are formed such that angle α may be smaller than angle β. Angle α may be in a range of about 20° to 30°. A range of 22° to 26° is preferred, with 24° presently believed to be optimal. The angle β may be in a range of 30° to 37°. A range of 32° to 35° is preferred, with 33.5° presently believed to be optimal. With a two-region configuration, the region 11b' that directly penetrates into a body for securing its position may be less pointed than that of a conical continuation of the region 11a'. During the experiments for measuring the penetration depth of the pins, it was determined that the pins generally penetrate no more than 1.5 mm into a body. Thus, the conical penetration region 11b' preferably has a minimum length of 1.5 mm in the direction of the axis 14.

New CT scans were taken using a TECAMAX SRP pin and an SNI 750 pin exhibiting the geometry shown in FIG. 9A, yielding unexpected results. The less pointed fastening device 7' created fewer artifacts in the CT scan recordings. Also noted was that small deviations in the angles α and β do not produce substantial differences in the extent of artifacts.

Figure 10A:
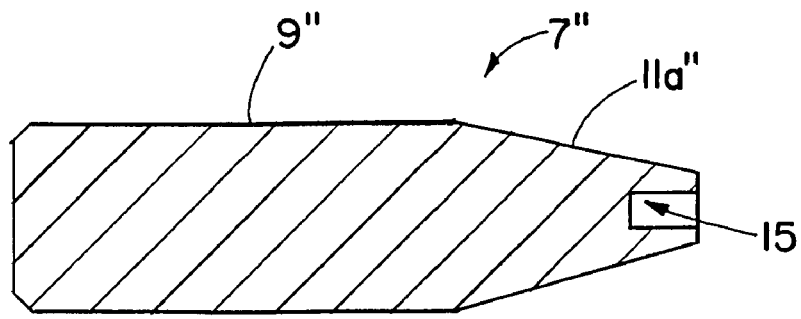
FIGS. 10A and 10B show schematic representations of an exemplary pin in accordance with the invention in which a penetrating portion is formed in two pieces.
Figure 10B:
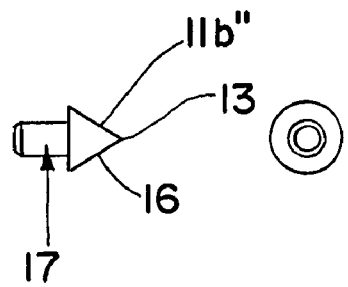

While the pin 7' shown in FIG. 9A may be formed in one piece and may be manufactured from a single material, FIGS. 10A and 10B show an exemplary schematic sectional representation of a hybrid pin 7" that is formed from at least two pieces. The first piece may include a holding portion 9" and a first region 11a" of a penetrating portion 11". The first region 11a" of the penetrating portion 11" may include a hollow space 15, which is cylindrical in the example shown. A second region 11b" of the penetrating portion 11" can be formed such that it can be at least partially inserted into the hollow space 15. The first and second regions may be assembled and held together by press-fit, adhesion, injection molding, or other acceptable method. The second region 11b" of the penetrating portion 11" may be formed in one piece of one material. The material may be the same or different from the material of the first region 11a". Alternatively, the second region 11b" may be formed from two pieces. A two piece second region 11b" may include a head piece 16, which may be conical and includes a tip 13, and a continuation piece 17 which is shown as cylindrical in the present example. The continuation piece 17 may be inserted into the hollow space 15. When assembled, the dimensions, proportions, and angles of a two-piece or hybrid pin 7" shown in FIGS. 10A and 10B correspond to the dimensions, proportions, and angles of the pin 7' shown in FIG. 9A. In other words, the penetrating portion 11' including regions 11a' and 11a" correspond to penetrating portion 11" including regions and 11b' and 11b". Angles α and β with respect to axis 14 of pin 7' also correspond to the same angles of pin 7", wherein the angle α in both designs is smaller than the angle β in both designs.

Figure 10C:
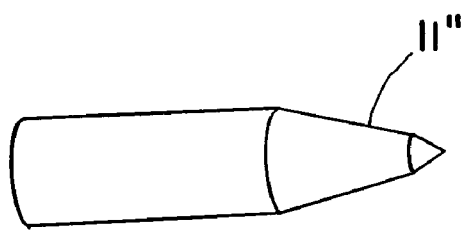
FIG. 10C shows an illustration of a pin corresponding FIGS. 10A and 10B.

One advantage of the hybrid pin 7" shown in FIGS. 10A and 10B is that the holding portion 9" and the first region 11a" of the penetrating portion 11" can be manufactured from a first material, and the second region 11b" of the penetrating portion 11" can be manufactured from another material. For example, the second region 11b" of the penetrating portion 11" may be a ceramic material while the remainder of the fastening device 7" (including the holding portion 9" and the first region 11a" of the penetrating portion 11") can be produced from another material (for example, TECAMAX SRP). A prototype of such a hybrid pin is shown in FIG. 10C.

Figure 11A:
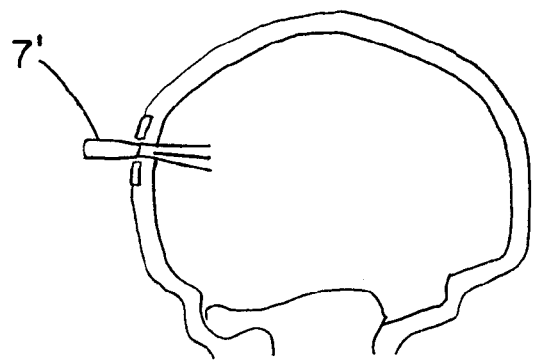
FIGS. 11A to 11C show exemplary x-ray tomograms of a cranial phantom filled with gel, wherein exemplary pins in accordance with the invention made of different materials are fastened to the skull.
Figure 11B:
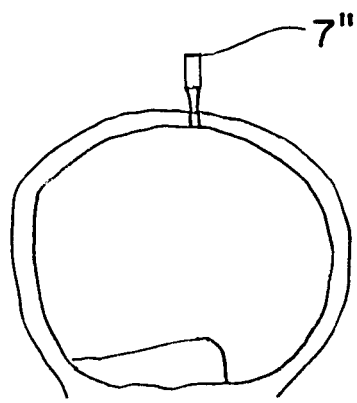
Figure 11C:
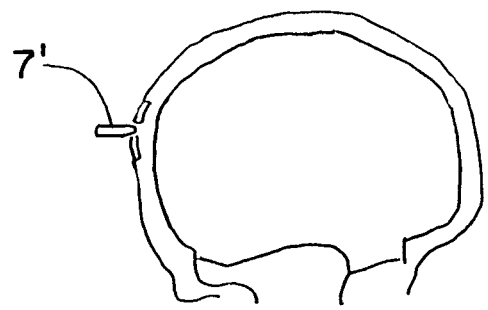

Pins 7' made of the materials TECAMAX SRP and SNI 750, which were formed in one piece and exhibit the geometry shown in FIG. 9A, were tested for artifact creation. A hybrid pin 7" as shown in FIGS. 10A through 10C was also tested for artifact creation. The exemplary hybrid pin 7" included a second region 11b' of the penetrating portion together with the tip 13 made from SNI 750, while the remainder of the hybrid pin 7" including the holding portion 9" and the first region 11a" of the penetrating portion 11" was made from TECAMAX SRP. A series of CT-scans were taken of each pin configuration. Several exemplary scan recordings are shown in FIG. 11A through 11C. FIG. 11A shows an SNI 750 pin 7' exhibiting the geometry of FIG. 9A. FIG. 11B shows a hybrid pin 7" exhibiting the geometry of FIGS. 10A and 10B and made from a combination of TECAMAX SRP and SNI 750. FIG. 11C shows a TECAMAX SRP pin 7' exhibiting the geometry of FIG. 9A. The scan recording shown in FIG. 11A shows minor artifacts but is very readable and the recordings shown in FIG. 11B and FIG. 11C are almost free of artifacts and are high-quality recordings. By comparing FIG. 11A (a complete SNI 750 pin) with FIG. 11C (a hybrid pin of SNI 750 with TECAMAX SRP), it can be seen that by producing a hybrid pin, in which the greater region is produced from TECAMAX SRP, the positive artifact properties of TECAMAX SRP dominate its performance. Thus, for good properties with regard to the creation of artifacts, it is not necessary for the pin used to be produced completely from a material which is particularly good at suppressing artifacts.

Figure 12A:
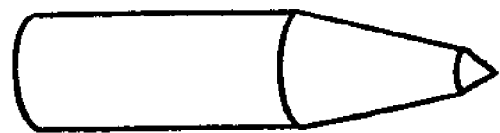
FIGS. 12A an 12B show exemplary pins in accordance with the invention, after they have been used in a head clamp, wherein the pins shown exhibit the geometry shown in FIG. 9A.
Figure 12B:
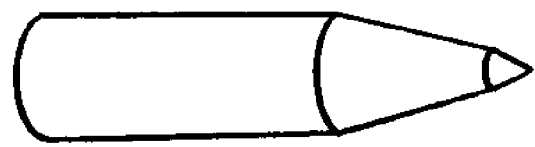

The pins used for the recordings shown in FIG. 11 were subjected to mechanical load tests. The tests were run in the same manner as the first series of experiments. In summary, the pins 7' made of TECAMAX SRP and SNI 750 performed better than the original pins 7 that did not have the geometry of FIG. 9A. FIG. 12A shows a TECAMAX SRP 7' pin and FIG. 12B shows an SNI 750 7' pin, each displaying the maximum damage received in the second series of tests. In both cases, almost no deformation or defect can be seen. In comparison, the hybrid pin had noticeable deformation and damage.

Figure 13:
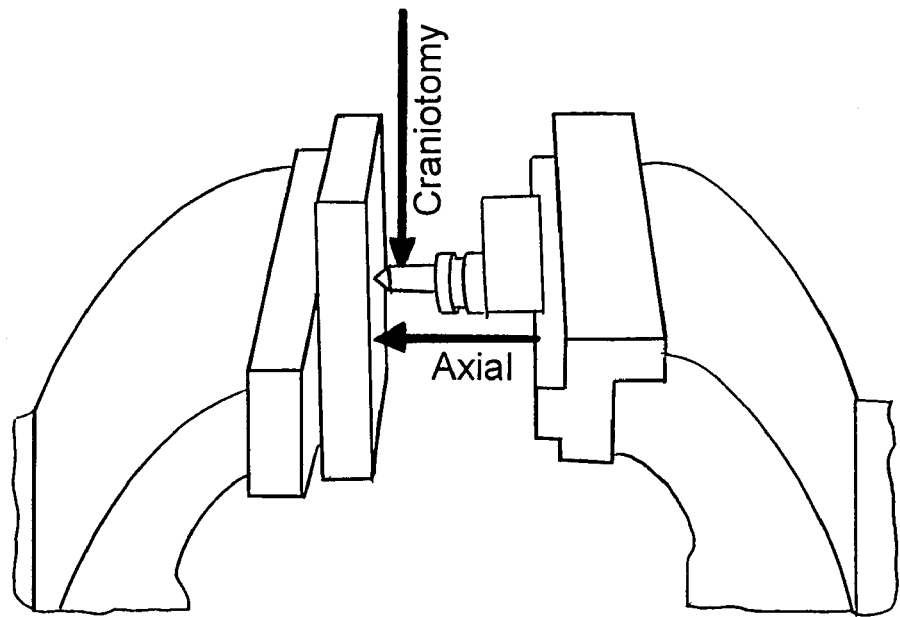
FIG. 13 shows an experimental design for testing axial loads on pins.
Figure 14A:
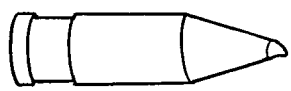
FIGS. 14A to 14D show exemplary pins in accordance with the invention after the load test, performed using the arrangement shown in FIG. 13.
Figure 14B:
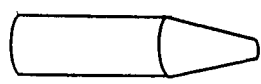
Figure 14C:
Figure 14D:
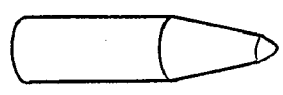

To more precisely gage the pins' resistance to mechanical stress, the pins were clamped into an experimental arrangement as shown in FIG. 13. When clamped in position, the pins were compressed with an axial force that was measured by a sensor. The maximum effective force applied to the pins was 2,000 N. A force of this magnitude corresponds to a safety factor of more than 5.5 over the actual forces experienced by a pin during a craniotomy. During the experiment, the pins were pressed against an aluminum plated to simulate the bone of a patient. As the aluminum plate is substantially harder than a human bone, the tests subject the pins to a higher stress than the pins will receive in actual craniotomies.

Four variations of pins were subjected to the FIG. 13 test. The variations include pins 7' made from TECAMAX SRP and pins 7' made from SNI 750, a hybrid pin 7" made from a combination of TECAMAX SRP and SNI 750, and a titanium pin for baseline purposes. After the tests were conducted the pins were visually examined and exemplary pins are shown in FIGS. 14A through 14D. The titanium pin shown in FIG. 14A withstood the axial force of 2,000 N; it was merely deformed slightly in the region of the tip. The SNI 750 pin shown in FIG. 14C and the TECAMAX SRP pin shown in FIG. 14D also withstood the axial force of 2,000 N. The hybrid pin (FIG. 14B), however, fractured at an axial force of 400 N. Based on this fracture at extremely high loads, it is recommended that the exemplary hybrid pin should be used at locations pin 2 and pin 3 as these locations bear significantly lower forces than pins located at pin 1.

Figure 15:
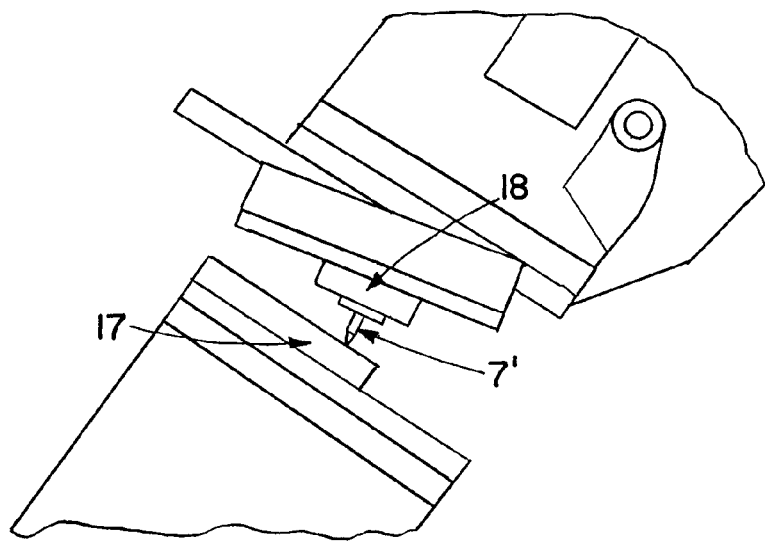
FIG. 15 shows an experimental design for testing pins by applying axial loads in combination with bending moments.
Figure 16A:
FIGS. 16A and 16B show exemplary pins made of different materials, after performing the test using the arrangement shown in FIG. 15.
Figure 16B:
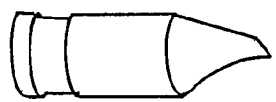

In another test, the pins 7' made of TECAMAX SRP and SNI 750 and a comparative pin made of steel were subjected to an experiment in which bending moments were applied in addition to the large axial forces. FIG. 15 shows an experimental arrangement in which a pin 7' is pressed obliquely onto a surface 17. The applied axial force was measured using a sensor 18. A pin made of TECAMAX SRP (FIG. 16A) fractured at an applied axial force of 1,850 N. This force value is well above the forces actually occurring during a craniotomy. The steel pin shown in FIG. 16B did not fracture at an applied axial force of 2,000 N.

Its tip, however, was deformed. The SNI 750 pin was tested and the results were similar to the steel pin.

Figure 18:
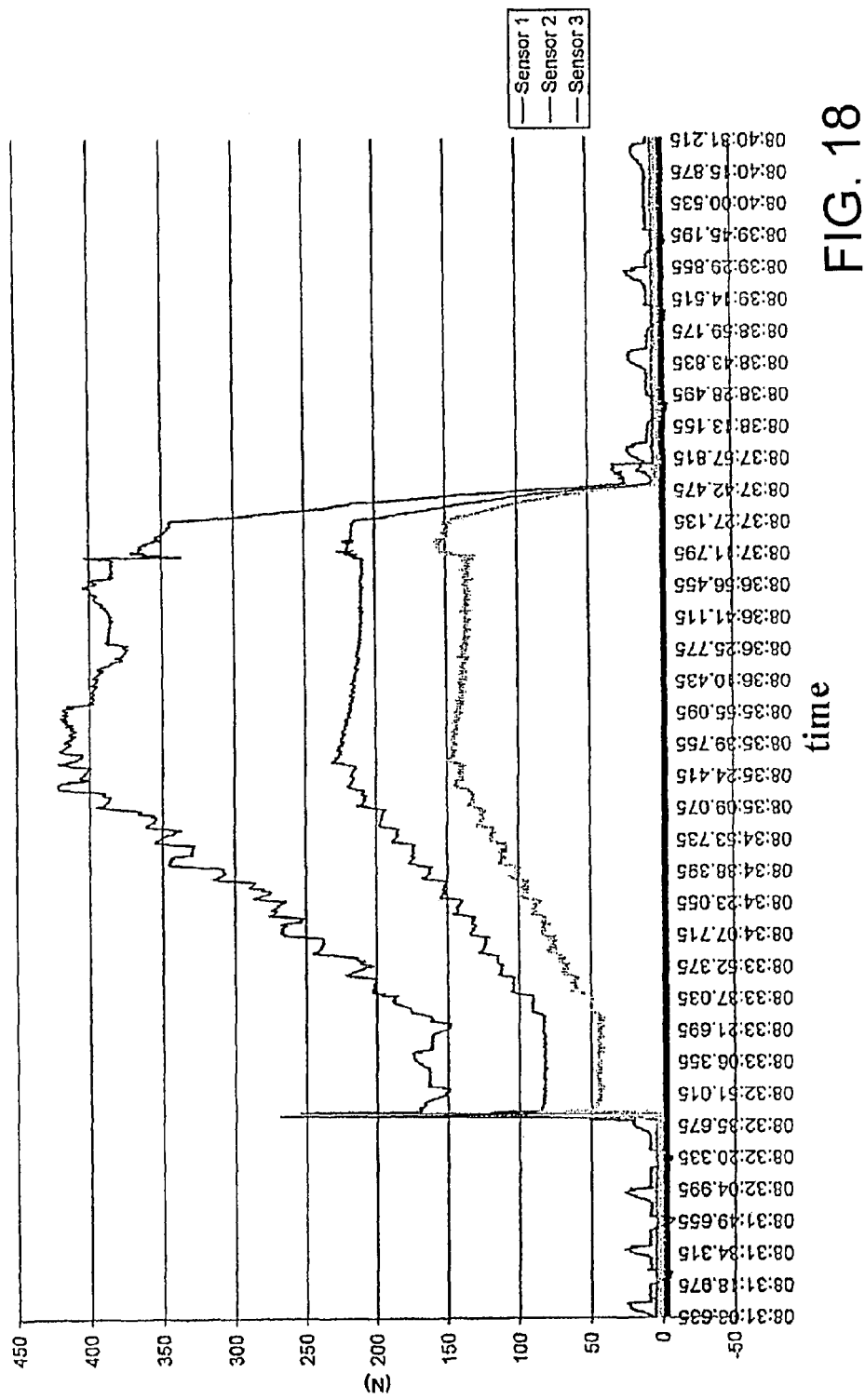

The series of experiments conducted in the pathology institute by neurosurgeons on cadavers was repeated with a new geometry pin 7' and a hybrid pin 7" in a manner consistent with surgical conditions. The head was first secured and was then moved to test the securement, and the head clamp was loosened to release the head. The pins, once removed from the head clamp, were examined. In FIGS. 17 and 18, measurements of the applied axial force as are plotted over time. A pin made of silicon nitride and exhibiting the improved geometry was used in FIG. 17. A hybrid pin (TECAMAX SRP and SNI 750) was used in FIG. 18. The forces occurring do not differ in principle from those obtained when using a pin exhibiting the original geometry (see FIGS. 6A through 6H).

A summary of the results from the second series of experiments are shown below in Table 4:

TABLE 4

| Material | 1 | 2 | 3 | 4 | Ranking |
| --- | --- | --- | --- | --- | --- |
| SNI 750 | ++ | ++ | ++ | 0 | $2^{nd}$ |
| hybrid pin | ++ | + | − | + | $3^{rd}$ |
| TECAMAX SRP | ++ | ++ | + | ++ | $1^{st}$ |

Legend
1 = biocompatibility
2 = ability to be sterilized
3 = resistance to mechanical stress
4 = artifact creation Through the second series of experiments, the pin 7' made of TECAMAX SRP is observed to have the best overall test performance, closely followed by the pin 7' made of SNI 750. Moreover, the revised geometry pin 7' of FIG. 9A resisted mechanical stress better than the original geometry of pin 7. The pin 7' made of SNI 750 provides the best resistance to mechanical stress, closely followed by TECAMAX SRP. The pin 7' made of TECAMAX SRP provides excellent results with regard to artifact creation whereas the pin 7' made from SNI 750 provides satisfactory results.

In summary, all the materials mentioned in Table 4 provide significantly improved results as compared to the prior art for fastening devices for securing the position of a body. The improved results are attributed to the choice of material and the improved geometry.

Although the invention has been shown and described with respect to a certain exemplary embodiment or embodiments, it is obvious that equivalent alterations and modifications will occur to others skilled in the art upon the reading and understanding of this specification and the annexed figures. For example, regard to the various functions performed by the above described elements (components, assemblies, devices, etc.), the terms used to describe such elements are intended to correspond, unless otherwise indicated, to any element that performs the specified function of the described element (i.e., that is functionally equivalent), even though not structurally equivalent to the disclosed structure that performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A fastening device for securing the position of a part of a body during a medical procedure, comprising:
 a holding portion; and
 a penetrating portion connected to the holding portion and comprising a first region having the shape of a truncated cone adjacent the holding portion, and a second region having the shape of a cone extending away from said holding portion and ending in a tip, wherein an angle formed between a surface of the truncated cone with respect to a longitudinal axis of the truncated cone is different than an angle formed between a surface of the cone with respect to a longitudinal axis of the cone.

2. The fastening device according to claim 1, wherein the fastening device is configured for securing a head, the medical procedure comprises an operation, and the fastening device comprises unsubstituted, monosubstituted or multisubstituted polyparaphenylene.

3. The fastening device according to claim 2, wherein the fastening device comprises a polyparaphenylene copolymer.

4. The fastening device according to claim 1, wherein the fastening device comprises a polyparaphenylene copolymer, wherein:
 a first monomer is monosubstituted in the ortho position;
 a second monomer is monosubstituted in the meta position; and
 a substituent in each case is a benzoyl group.

5. The fastening device according to claim 1, wherein the penetrating portion and/or the holding portion are rotationally symmetrical around a longitudinal axis of the fastening device.

6. The fastening device according to claim 1, wherein the longitudinal axis of the truncated cone is colinear with the longitudinal axis of the cone.

7. The fastening device according to claim 1, wherein:
 the penetrating portion comprises a first piece and a second piece, and the first piece is securely connected to the second piece and comprises a tip on an end opposite the second piece.

8. The fastening device according to claim 7, wherein the tip comprises silicon nitride ceramic.

9. The fastening device according to claim 1, wherein at least one of the holding portion or the penetrating portion comprises silicon nitride ceramic.

10. The fastening device according to claim 9, wherein the fastening device is configured for securing a head, the medical procedure comprises an operation, and the fastening device comprises β silicon nitride ceramic.

11. The fastening device according to claim 9, wherein the penetrating portion and/or the holding portion are rotationally symmetrical around a longitudinal axis of the fastening device.

12. The fastening device according to claim 9, wherein the longitudinal axis of the truncated cone is colinear with the longitudinal axis of the cone.

13. The fastening device according to claim 9, wherein:
 the penetrating portion comprises a first piece and a second piece, and
 the first piece is securely connected to the second piece and comprises a tip on an end opposite the second piece.

14. The fastening device according to claim 13, wherein the first piece comprises silicon nitride ceramic.

15. The fastening device according to claim 1, wherein at least one of the holding portion or the penetrating portion comprises unsubstituted, monosubstituted or multisubstituted polyphenylene.

* * * * *